United States Patent [19]

Schultze

[11] Patent Number: 4,623,624
[45] Date of Patent: Nov. 18, 1986

[54] ISOLATION OF PANCREATIN

[75] Inventor: Hans Schultze, Moorrege, Fed. Rep. of Germany

[73] Assignee: BASF Aktiengesellschaft, Ludwigshafen, Fed. Rep. of Germany

[21] Appl. No.: 565,220

[22] Filed: Dec. 23, 1983

[30] Foreign Application Priority Data

Dec. 30, 1982 [DE] Fed. Rep. of Germany ....... 3248587
Dec. 30, 1982 [DE] Fed. Rep. of Germany ....... 3248588

[51] Int. Cl.$^4$ .......................... C12N 9/94; C12N 9/64
[52] U.S. Cl. .................................. 435/186; 435/226
[58] Field of Search .................. 435/226, 186, 22, 23, 435/39, 259, 94, 816; 436/70, 17; 424/110

[56] References Cited

U.S. PATENT DOCUMENTS 3,223,594 12/1965 Hoek et al. ............................ 195/68
4,088,539 5/1978 Müller ................................... 195/66

FOREIGN PATENT DOCUMENTS 1328202 8/1973 United Kingdom .

*Primary Examiner*—Lionel M. Shapiro
*Assistant Examiner*—Rebecca L. Thompson
*Attorney, Agent, or Firm*—Keil & Weinkauf

[57] ABSTRACT

Highly active pancreatin is obtained by autolysis of an aqueous isopropanol-containing tissue slurry, preferably buffered with sodium bicarbonate, until a test precipitation with aqueous isopropyl alcohol proves positive, and precipitating the batch with a higher concentration of isopropyl alcohol, resulting in a fiber suspension which can be sieved so that the solution obtained permits direct isolation of pancreatin by further increasing the concentration of isopropyl alcohol. A high bulk density of the finished dry preparation is achieved by stirring the precipitated pancreatin with isopropyl alcohol or acetone so as to bring the pancreatin to a concentration of 70–85% of isopropanol or 80–95% of acetone, isolating the pancreatin by suction filtration or centrifuging and drying it by treatment with dry air or nitrogen.

5 Claims, No Drawings

ISOLATION OF PANCREATIN

Pancreatin is the mixture of enzymes obtained by extraction of the pancreas and consisting essentially of lipases, amylase and proteases. Pancreatin is used as an active compound for treatment of digestive disturbances attributable to pancreatic insufficiency. The starting material is in the main pig's pancreas, either fresh or frozen, from which originally only the water and fat had been removed. However, because of the sensitivity of the enzymes such removal has hitherto had to be carried out very cautiously.

In the processes which are conventionally used to this day, drying and defatting are carried out with solvents which dissolve water and fat simultaneously, for example acetone or higher alcohols. In other known processes, the two procedures are effected successively, the drying (freeze-drying) mostly being carried out first, followed by defatting with a volatile solvent for fats, though the process can be carried out in reverse, namely defatting in the liquid phase using hydrocarbons or halohydrocarbons, followed by drying of the aqueous phase.

All pancreatin formulations produced by one of these processes have the disadvantage that the proteases, e.g. trypsin and chymotrypsin, are not present in them in the free form but in their inactive enzymogen form. They can therefore not become active in the very patients who do not produce enterokinase in the body itself, and are accordingly completely inactive. A further disadvantage is the fiber content of these pancreatins, which originates from the connective tissue of the pancreas and is of no medical value. This fiber content not only interferes with tableting when producing pharmaceutical preparations, but also hinders the desired disintegration of the tablet at the site where it is to become active, so that the enzymes remain largely unutilized.

Certain more recent processes already take account of this information. The fibers are removed and an autolysis is carried out to produce activated enzymes. However, the autolysis not only releases but also damages the enzymes. Consequently, a full enzyme yield is not obtainable in these processes.

The autolysis is carried out in a great variety of ways. For example, in the process of U.S. Pat. No. 3,223,594 autolysis is conducted for 2 hours at room temperature in the presence of a large amount of water, whereas in the processes of German Laid-Open Applications Nos. DOS 2,620,289 and DOS 2,716,719 autolysis is effected for 15 hours at 15° C. or 4 hours at 15° C. respectively, in the presence of water-immiscible solvents for fats. According to the description in British Patent No. 1,328,202 the autolysis is effected in ½–2 hours at 20°–30° C., in the presence of sodium hydroxide or ammonia. German Published Application No. DAS 2,106,706 describes an autolysis which, in order to improve the enterokinase activity, extends over 7 days at 4° C., in the presence of pig's duodenum.

U.S. Pat. No. 3,223,594 describes a yield of 11% by weight, with enzyme units of as high as $10 \times NF$, which corresponds to about 69% of the possible enzyme yield, since in general 100 g of pancreas tissue, when dried without loss and defatted, give 20 g of pancreatin in a quality of $8 \times NF$.

British Patent No. 1,328,202 reports a quality of $6-10 \times NF$, at a weight yield of sterile-filtered pancreatin of 3.4%, which thus corresponds to only 13–21% of the theoretically possible enzyme yield. German Laid-open Applications Nos. DOS 2,620,289 and DOS 2,716,719 report a full enzyme yield only in respect of lipase, while the yields of amylase and of proteases were evidently so much lower that the product is not even described as pancreatin any longer, but as a "lipase-rich enzyme preparation".

The theoretically possible yield of activated enzymes has thus hitherto evidently not been achieved. Moreover, no data has yet been given concerning the degree of protease activation, which per se can be determined by comparing the protease activity with and without enterokinase activation. Without activation, Less than 0.5 FIP-U/mg is found.

In the description of the prior art given above, NF stands for National Formulary, the official American Pharmacopeia, published by the American Pharmaceutical Association. On page 514 of the 13th edition (NF XIII), pancreatin is described as an enzyme-containing substance, the amylase activity of which suffices to convert at least a 25-fold weight of potato starch into soluble carbohydrates and also to proteolyze a 25-fold weight of casein. Pancreatins of greater digestive capacity are identified with a corresponding multiplication factor.

Thus, for example, 4-fold NF (or $4 \times NF$) means a pancreatin which contains so much amylase, proteases and lipase that 1 g of this pancreatin can catalyze the conversion of (4 times its 25-fold weight =) 100 g of the particular substrate (starch, casein or olive oil).

The definition of the FIP units is given by the "Commission on Pharmaceutical Enzymes" under the aegis of the "Fédération Internationale Pharmaceutique" (=FIP) in the monograph entitled "Pharmaceutical Enzymes" by R. Ruyssen and A. Lauwers, 1978, Scientific Publishing Company, Ghent/Belgium. Page 22 contains the general statement that 1 FIP-U catalyzes the conversion of 1 micromole or 1 microequivalent of substrate per minute under otherwise well-defined external conditions or—in cases where the substrate is chemically insufficiently defined—produces 1 micromole or 1 microequivalent of reaction product per minute. The external conditions to be used in determining the individual enzymes are described on pages 21 to 84.

The FIP units are thus determined by measuring the catalyzed initial reaction rate and can therefore also be determined more rapidly (and more accurately) than the NF-multiplicity conventionally employed at an earlier date.

A useful conversion table of FIP-U to x-fold NF-quality (experimentally determined) is given below; this also covers lipase units though NF XIII does not describe a lipase determination. It is assumed that a pancreatin preparation which in respect of amylase was analyzed, for example, to be 6-fold NF, is also 6-fold NF in respect of proteases and lipase, i.e. the ratio of the activities of the enzymes in natural pig's pancreas and in the pancreatin preparation obtained therefrom is assumed to be the same.

The practical usefulness of stating the NF factor is that a single numeral thus expresses the pancreatin quality in respect of the activity of all the enzymes contained therein.

The following correspondence is based on experience:

---

1-fold NF = 6,250 FIP-U of amylase per g of pancreatin

= 5,000 FIP-U of lipase per g of pancreatin
= 375 FIP-U of trypsin per g of pancreatin
= 1,250 FIP-U of chimotrypsin per g of pancreatin Doubling the FIP values corresponds to 2-fold NF etc.

In the processes hitherto disclosed, which start from an autolysate, the pancreatin is never obtained in a form which can readily be converted further. Processes by which pancreatin, in particular of high bulk density, is obtained directly from pancreas also do not exist, strictly speaking; at best, the production of an "lipase-rich enzyme preparation" in accordance with the above DOS's could be regarded as such, but it involves considerable technical effort and 3 different solvents.

It is an object of the present invention to provide a very simple and safe process by which, without major technical effort and with achievement of full enzyme yield, pancreatin of maximum enzyme activity and containing free proteases is obtained, which pancreatin moreover has a low germ count, is free-flowing, has a high bulk density, is free from fibers and can be processed and stored virtually without loss of enzymes, the essential steps in said process being the autolysis of an aqueous pancreas tissue slurry or aqueous tissue suspension, which slurry or suspension may or may not contain calcium ions, removal of the fibrous constituents and, if desired, dehydration, defatting, precipitation and drying of the precipitate obtained.

According to the invention, this object is achieved if the autolysis is carried out at below 30° C., with or without addition of up to 20% by weight of isopropyl alcohol, based on the suspension, at a pH of from 6.5 to 8.5, preferably in the presence of a buffer which gives a pH of from 6.5 to 7.5, for example of up to 3%, and especially of from 1 to 1.5%, of an alkali metal bicarbonate, these percentages being based on tissue employed, and in the presence or absence of a small amount of a calcium salt, and is stopped as soon as a sample of the autolysis suspension in 55–65% strength aqueous isopropyl alcohol gives a sedimentation rate of about 3–10 mm in 1–3 minutes. These figures relate to free sedimentation under gravity, i.e. without centrifuging.

The autolysis is stopped by adding isopropyl alcohol to the greater part of the autolysate, up to a concentration of 30–35% by weight, based on the sum of water and isopropyl alcohol; the autolyzate which as a result of this acquires a low viscosity can be separated from the connective tissue fibers by sieving. It is introduced, at 15°–25° C., into isopropyl alcohol so as to give a 55–65% strength solution, again based on the sum of water and isopropyl alcohol, from which the pancreatin precipitates in coarse granular form and sediments immediately. After siphoning off the supernatant liquor, the sedimented pancreatin can be washed free from fat and tryptone by repeatedly stirring it with isopropyl alcohol and allowing the mixture to settle. The precipitate should ultimately have a final isopropyl alcohol concentration of from 70 to 85% by weight, preferably from about 75 to 76% by weight, and can be isolated by suction filtration or by centrifuging, preferably under reduced pressure, and then be dried by treatment with dry air (for example containing less than 20% relative humidity at 20° C.) or with nitrogen. The washing of the precipitate, described above, can also be carried out with acetone in place of isopropyl alcohol.

Where, in the above statements concerning the alcohol content of the aqueous solutions or supernatant liquors, the weight of raw material employed enters into the calculation, the water content of this raw material is assumed to be 63% by weight.

Especially as regards the last-mentioned final isopropanol concentration in the precipitate, it is to be borne in mind that the establishment of equilibrium between the precipitate and supernatant liquor may take a very long time, since protein materials retain water very tenaciously and hence a water-enriched phase initially persists within the precipitated particles. Hence, these final concentration data also do not relate to the analytical composition of the solution phase but are calculated as stated above.

In practice, the process according to the invention is carried out as follows: the pancreas, which has been minced or chopped up, is mixed with from 20 to 80% of water to make the material easier to stir. The autolysis process is gently, i.e. without damage to the enzymes, directed in the desired manner, and accelerated, by use of about 1–1.5% of sodium bicarbonate; addition of more than 3% of bicarbonate may reduce the shelf life of the pancreatin. Addition of a small amount (for example less than 1%) of a calcium salt favors the autolysis. As the proteases are separated from their pro-enzymes, the digestion of the concomitant pancreas proteins initially accelerates due to the constantly increasing amount of free proteases.

However, this digestion would ultimately extend to the sensitive enzymes, so that especially amylase and also the proteases themselves would become damaged. Up to 20% of isopropyl alcohol, preferably from about 10 to 15%, is added to the mixture specifically to protect the proteases. This addition by itself however does not suffice to retain the enzyme activities completely. It is therefore important to discover the point in time, shortly before damage to the enzyme starts, at which the autolysis may most advantageously be stopped. In fact, the duration of autolysis up to this point may, under otherwise completely identical conditions, vary by up to 600% depending on the origin, age and conditions of storage of the pancreas, so that it is not possible to specify a generally valid autolysis duration.

According to the invention, the most advantageous point in time can be ascertained by using a simple quick test on a sample of the autolysate to determine the optimum sedimentation rate (settling rate) in 55–65% strength isopropyl alcohol. This sedimentation test virtually constitutes further processing of small samples of the autolysate up to the point of pancreatin precipitation and observation of their constantly varying sedimentation characteristics. To do this it is possible, for example, to take 10 g of the autolysate suspension at intervals of ½ hour—or, towards the end of the autolysis, for example every 10 or 15 minutes—stir these samples with 5 ml of 84% strength isopropyl alcohol and pour the resulting solution, with stirring, into 20 ml of 84% strength isopropyl alcohol. The sedimentation rate of the precipitate formed is determined. If, after a settling time of 3 minutes in a 50 ml beaker a clear upper layer of, for example, more than 3–5 mm is discernible, it means as a rule that the optimum sedimentation rate has been reached and so has the desired point in time before enzyme damage occurs. The incipient enzyme damage can be recognized from the fact that the supernatant liquor (i.e. the upper layer) is no longer clear or that the sediment is separated from the supernatant liquor by a cloudy zone.

To achieve more uniform autolysis characteristics of different batches it is advantageous to add a small amount of pancreatin from an earlier batch.

The autolysis can be carried out at from −2° to +30°, preferably at below 25° C., though it is not necessary to maintain a constant temperature. These low temperatures are useful in many ways, for example in that they save energy, permit autolysis to be carried out overnight and at weekends, and save labor. The most advantageous end point is in each case detected by the sedimentation test.

Further isopropyl alcohol is then added to the entire batch in order to stop the autolysis. In the process according to the invention, brief stirring of the mixture at 30-35% isopropyl alcohol content (based on water plus alcohol) gives an almost clear solution which is so mobile, apart from the undissolved fibers, that the fibers can be separated off without any problems whatsoever, even in the case of large batches, by sieving through a basket of 4-5 mm mesh width, preferably equipped with a stirrer, so that ultimately only a dry fiber residue is left. To precipitate the pancreatin, the sieved solution is run into isopropyl alcohol which may be of 80-100% strength but is present in such amount that after mixing with the 30-35% strength solution a precipitation concentration of 55-65% of isopropyl alcohol results. So-called 84% strength isopropyl alcohol which is recovered from aqueous solution and —approaching the azeotropic content of 88% by weight—contains about 84% of alcohol may be used advantageously.

At concentrations of less than 55% the precipitation is incomplete and would therefore entail a loss of yield. At above 65% undesired enzyme inhibitors are presumably also precipitated thereby apparently lowering the activity of the proteases.

The pancreatin precipitate obtained by the process of the invention is so coarse that it settles out within one hour to 10-20% of the original volume and the clear supernatant solution can simply be siphoned off or pumped off. The precipitate which has settled out can be washed simply by stirring with recovered 84% strength isopropyl alcohol and finally with fresh absolute isopropyl alcohol, in each case followed by renewed sedimentation. It is true that this sedimentation method has already been disclosed in British Patent No. 1,328,202 but did not acquire any importance because in most cases the sedimentation proved unsuccessful. Only by the sedimentation test according to the present invention has a reliable process been achieved.

At this stage, other, conventional, methods would employ a closed centrifuge with an inert gas blanket; this method damages the product due to a temperature rise, requires substantially longer for the separation and permits washing of the pancreatin only after thorough comminution in fresh solvent (entailing the danger of local superheating) and subsequent renewed centrifuging, consuming a great deal of energy and time.

The isopropyl alcohol can be recovered from the siphoned-off residues by distillation. The distillation residue separates into a lower aqueous layer which contains tryptones and soap in solution, and on top of which floats a layer of fat which solidifies after cooling. The recovered 84% strength isopropyl alcohol can be reused direct at any point of the process according to the invention.

Adjusting the isopropyl alcohol to 70-85% is advantageous for the drying process described below; in place of isopropyl alcohol, it would also be possible to use acetone at a concentration of 80-95%, in which case however the solvent would have to be changed.

The pancreatin sedimentation residue obtained can be filtered off extremely easily and hence it is simplest to use a suction filter. Of course, it is also possible to use an automatic filter or automatic centrifuge. The residue can be made storable by conventional methods, for example by freeze-drying; preferably, however, the following method is employed:

During drying of the cake, which contains adhering mother liquor itself containing about 70-85%, preferably 75-80%, of isopropyl alcohol, a large contraction in volume is observed. This shrinkage process leads to a pancreatin of high bulk density (0.5-0.7 g/ml) which, after coarse grinding, forms easily pourable particles. If on the other hand the pancreatin to be dried contains significantly more than 85-86% of isopropyl alcohol, no contraction results and the product formed has such a low bulk density (0.2 g/ml) that it easily acquires electrostatic charges and is therefore difficult to handle. If on the other hand the pancreatin to be dried contains isopropyl alcohol of less than 70% strength, the desired contraction in volume does occur but the lipase suffers some damage even if the drying is carried out at 0° C. under reduced pressure. Enzyme damage may also occur if drying is carried out at above 25° C. or if, with or without the use of reduced pressure, drying is carried out in air containing more than 20% of relative humidity at 20° C. The above data depend somewhat on the actual content of isopropyl alcohol.

The pancreatin produced according to the invention has a low germ count. The germs remain very largely in the fibers which are sieved out of the pancreatin solution. Moreover, treatment with isopropyl alcohol at the required concentration is a known means of killing germs, especially because the spores which may be present in the initially purely aqueous suspension pass, during autolysis, into their sensitive vegetative form.

The good stability of the pancreatin prepared according to the invention is made clear by an exposure test which simulates subsequent conversion to coated tablets: the pancreatin is first stored for 20 hours with free exposure to air at 20° C. and 58% relative humidity and is then heated at 50° C. in a closed vessel for 24 hours.

TABLE 1

Comparison of the amylase and lipase stability of pancreatins respectively prepared according to the prior art and according to the novel process. Pancreatins 1, 2 and 3 are commercial preparations from different manufacturers.

| Method of preparation | Amylase initial activity in FIP-U/mg | Loss on treatment described | Lipase initial activity in FIP-U/mg | Loss on treatment described |
|---|---|---|---|---|
| 1. Prior art | 43.1 | 6% | 40.7 | 7% |
| 2. Prior art | 57.2 | 43% | 37.0 | 14% |
| 3. Prior art | 51.0 | 41% | 48.3 | 31% |
| 4. Novel process | 93.6 | 3% | 90.3 | 6% |

Table 1 shows that in conventional pancreatins the losses during the treatment described increase greatly with enzyme activity. Surprisingly, however, the pancreatin prepared by the novel process shows the lowest loss on such treatment, in spite of its substantially higher enzyme activity.

EXAMPLE 100 kg of deep-frozen pig's pancreas are minced or chopped and stirred in a 250 liter kettle with a solution of 100 g of calcium gluconate in 20 liters of water together with 200 g of silicone anti-foam agent.

Depending on the content of free trypsin in the pancreas, up to 1 kg of previously prepared pancreatin, dissolved in 5 liters of water, are added as a starting aid for autolysis. This amount of pancreatin to be added is determined by the "37° hydrolysis test" described later. To carry out this test, 120 g are taken from the batch at this stage.

After addition of 15 liters of 84% strength isopropyl alcohol, a solution of 1.5 kg of sodium bicarbonate in 20 liters of water is also stirred into the batch. The latter is left to stand overnight, in the course of which the temperature rises from about 2° to 12°, and next morning the batch is warmed to 20° C. and stirring is continued at this temperature.

The end point of the autolysis is detected by the sedimentation test. For this purpose, during this last stage of the autolysis 10 g samples of the suspension are taken initially every 30 minutes and later on every 15 minutes, and are stirred for one minute with 5.4 ml of 84% strength isopropyl alcohol, using a glass rod; the resulting solution is separated from the fibers sticking to the glass rod and is stirred into 20 ml of an 84% strength aqueous isopropyl alcohol solution contained in a 50 ml beaker with magnetic stirrer. After one minute, the stirrer is switched off and the mixture is left to settle for one or three minutes.

The sample is rated as positive, and the autolysis is therefore stopped, if 3 mm of a more or less clear supernatant layer are discernible in one minute or 10 mm in 3 minutes.

As an example, we give below a typical sedimentation test series started as soon as the autolysate is at 20° C.

| Autolysis time at 20° C. | Sedimentation test | | |
|---|---|---|---|
| | mm/0.5 min | corresponds to mm/1 min | corresponds to mm/3 min |
| 1.00 hour | 0 | 0 | 0 |
| 2.00 hours | 0 | 0 | 0 |
| 2.50 hours | 0 | 0 | 1 |
| 2.75 hours | 0 | 1 | 4 |
| 3.00 hours | 1 | 3 | 10 |
| 3.25 hours | 3 | 6 | 18 |
| 3.50 hours | 5 | 10 | 20 |
| 3.75 hours | 9 | 18 | 20 |
| 4.00 hours | 14 | 20 | 20 |

In this example, the most advantageous point for stopping the autolysis is therefore reached after 3 hours. In order that this should also allow comparable conditions to be achieved, at least approximately, when using a different and unknown pig's pancreas preparation (for example a preparation which has been stored for a longer or shorter period), the 37° hydrolysis test is carried out: 120 g are taken from the pancreas slurry mixed with Ca gluconate, 1.5 g of sodium bicarbonate in 25 ml of water are added and the mixture is stirred for 30 minutes at 37° C. The sedimentation test is carried out with a sample of this high-speed autolysate. At less than 2 mm 3 minutes, 2 million U of free trypsin are added, at up to 12 mm/1 minute, 1 million U is added, and even higher sedimentation rates no free trypsin is added to the main batch (in the form of pancreatin). (1 million U of free trypsin are contained in, for example, 250 g of pancreatin of strength 4000 U/g). In this way, raw materials of different origin can be standardized for production operations.

After the most advantageous point in time has been determined, the autolysis is stopped by pumping 72.5 liters of 84% strength (recovered) isopropyl alcohol into the batch. The mixture is stirred for another 30 minutes, resulting in a clear solution plus undissolved fibers, which are then sieved off. To do so, the contents of the kettle are drained into an open 50 liter kettle provided with an anchor stirrer and having an inset sieve of about 5 mm mesh width. The bottom outlet of the sieving kettle is connected via a pump to a 500 liter polypropylene vessel. The latter is charged with 318 liters of recovered 84% strength isopropyl alcohol and is then filled with the drained-out sieved solution, while stirring slowly. The fibers left in the sieving kettle are stirred dry for a further 10 minutes. The weight of the fibers is 7–8 kg.

In the 500 liter vessel, the precipitated pancreatin settles out as a coarse precipitate, giving a volume of 80 liters in one hour at 20° C. or in half an hour at 24° C. The supernatant liquor is siphoned off and used for recuperative distillation. The sediment is stirred with 63 liters of recovered 84% strength isopropyl alcohol and is allowed to settle out again overnight. This process is repeated the next day, and the sediment thus formed is mixed with about 45 liters of 84% strength isopropyl alcohol, i.e. with the amount required to give a pancreatin suspension in 76% strength isopropyl alcohol. This suspension is filtered on a suction filter of 40 cm diameter and is thoroughly sucked dry.

The filter cake is briefly comminuted in a cutter and is spread on metal trays. It is dried overnight at up to 55° C. under reduced pressure, namely about 5 mbar.

Pancreatin yield: 11.6 kg
Amylase activity: 93.6 FIP-U/mg
Lipase activity: 90.3 FIP-U/mg
Protease activity activated
  with enterokinase: 5.6 FIP-U/mg
  without activation: 5.6 FIP-U/mg
Trypsin activity activated
  with enterokinase: 4.2 FIP-U/mg
  without activation: 4.1 FIP-U/mg
Chymotrypsin activity activated
  with enterokinase: 28.3 FIP-U/mg
  without activation: 28.3 FIP-U/mg
Solids content: 98.7%
Fat content: 0.4%
Bulk density: 0.65 g/ml
Tap density: 0.76 g/ml
Germ count: 200 germs/g no germs which are contrary to USP XVII

I claim:

1. A process for isolating pancreatin by autolysis of an aqueous pancreas tissue suspension, wherein the autolysis is carried out at below 30° C. with addition of up to 20% by weight of isopropyl alcohol, based on the suspension, at a pH of from 6.5 to 8.5, testing a sample of the autolyzed suspension to determine the sedimentation rate and stopping the autolysis as soon as a sample in 55–65% strength aqueous isopropyl alcohol shows a sedimentation rate, measured under gravity, of about 3–10 mm/1–3 minutes.

2. The process of claim 1, wherein the pH is adjusted by adding up to 3%, based on tissue employed, of an alkali metal bicarbonate.

3. The process of claim 1, wherein the autolysis is carried out in the presence of pancreatin from an earlier batch.

4. The process of claim 1, wherein the autolysis is stopped by adding isopropyl alcohol up to a concentration of as high as 30-35%, based on the sum of water and isopropyl alcohol, the batch which has acquired a low viscosity is sieved to remove connective tissue fibers, the solution is introduced, at 15°-25° C., into an amount of isopropyl alcohol such that an aqueous solution containing 55-65% by weight of isopropyl alcohol results, the precipitated pancreatin is allowed to sediment in granular form, the supernatant liquor is siphoned off and the pancreatin is washed free from fat and tryptone, if appropriate, by repeatedly stirring it with isopropyl alcohol and allowing it to sediment, and is dried.

5. The process of claim 4, wherein the pancreatin which has precipitated is allowed to sediment, the supernatant liquor is siphoned off or suction-filtered off, the pancreatin is washed free from fat and tryptone by, if appropriate, repeatedly stirring it with isopropyl alcohol or acetone until a precipitate having an isopropyl concentration of 70-85% or an acetone concentration of 80-95% results, and this precipitate is isolated by suction filtration or centrifuging and is dried by treatment with dry air or nitrogen at below 25° C., under reduced pressure.

* * * * *